United States Patent

Loverock

Patent Number: 5,998,389
Date of Patent: Dec. 7, 1999

[54] ENDOTOXIN-SPECIFIC ASSAY

[75] Inventor: Bruce Loverock, Thurmont, Md.

[73] Assignee: BioWhitaker Technologies

[21] Appl. No.: 09/081,659

[22] Filed: May 20, 1998

[51] Int. Cl.$^6$ .......................... A61K 31/715; C12Q 1/00; C12Q 1/04

[52] U.S. Cl. .......................... 514/54; 536/123.12; 435/4; 435/34; 436/63; 436/74

[58] Field of Search .................. 514/54; 536/123.12; 435/4, 34; 436/63, 74

[56] References Cited

U.S. PATENT DOCUMENTS

| | | | |
|---|---|---|---|
| 5,155,032 | 10/1992 | Tanaka et al. | 435/184 |
| 5,179,006 | 1/1993 | Matuura et al. | 435/23 |
| 5,641,643 | 6/1997 | Tanaka et al. | 536/123.12 |
| 5,702,882 | 12/1997 | Tamura et al. | 435/4 |

FOREIGN PATENT DOCUMENTS

| | | |
|---|---|---|
| 0 397 880 | 3/1990 | European Pat. Off. . |
| 0330 991 | 11/1994 | European Pat. Off. . |

OTHER PUBLICATIONS

Iwanaga, Current Opinion Immunology, vol. 5, pp. 74–82, 1993.

Kambayashi et al., J. Biochem. Biophys. Methods, vol. 22, pp. 93–100, 1991.

Cooper et al., PDA J. Pharm. Sci. Technol., vol. 51, pp. 2–6, 1997.

Product Brochure "Limulus Amebocyte Lysate Kinetic–QCL™ LAL Testing Made Easy 192 Test Kit" Catalog No. 50–650U, pp. 1–18, May 1996.

Product Brochure "Limulus Amebocyte Lysate Pyrogent®–5000" Catalog No. N383, N384, p. 1–20, May 1995.

G. Zhang et al. "Differential Blocking of Coagulation–Activating Pathways of Limulus Amebocyte" Journal of Clinical Microbiology, Jun. 1994 pp. 1537–1541.

T. Morita et al. "Biochemical Characterization of Limulus Clotting Factors and Inhibitors which Interact with Bacterial Endotoxins" Bacterial Endotoxins: Structure, Biomedical Signifcance, and Detection with the Limulus Amebocyte Lysate Test, pp. 53–64, 1985.

(List continued on next page.)

Primary Examiner—Gary L. Kunz
Assistant Examiner—Everett White
Attorney, Agent, or Firm—Banner & Witcoff, Ltd.

[57] ABSTRACT $\beta$-1,4-glucans, particularly cellobiose, can be used to inhibit the glucan-specific enzymatic pathway in an amebocyte lysate. So inhibited, the amebocyte lysate can then be used to specifically detect endotoxin in a test sample. $\beta$-1,4-glucan inhibitors can be used in a variety of amebocyte lysate assays, including kinetic-chromogenic, end-point chromogenic, turbidimetric, gel-clot, and ELISA assays.

24 Claims, 3 Drawing Sheets

The Effect of Cellobiose Concentration on the Glucan LAL Response

OTHER PUBLICATIONS

J: Kambayashi et al. "A novel endotoxin–specific assay by turbidimetry with Limulus amoebocyte lysate containing β–glucan" Journal of Biochem Biophys Methods 22 93–100 1991.

P.F. Roslansky & T.J. Novitsky "Sensitivity of Limulus Amebocyte Lysate (LAL) to LAL–Reactive Glucans" Journal of Clinical Microbiology, 1991, p 2477–83.

N. Ohno et al. "Reactivity of Limulus amoebocyte lysate towards (1→3)–βD–glucans" Carbohydrate Research, 207 (1990) 311–318.

S. Tanaka et al. "Inhibition of high–molecular–weight–(1→3)–β–D–glucan–dependent activation of a limulus coagulation factor G by laminaran oligosaccharides and curdian degradation products" Carbohydrate Research 244 5 (1993) 115–127.

S. Iwanaga "The limulus clotting reaction" Current Opinion in Immunology 5 (1993) p. 74–82.

Iwanaga et al. The Limulus Coagulation System Sensitive to Bacterial Endotoxins, in Bacterial Endotoxin Chemical, Biological and Clinical Aspects, pp. 365–382 (1984).

J. Cooper et al. "The Impact of Non–endotoxin LAL–Reactive Materials on Limulus Amebocyte Lysate Analyses" Journal of Pharmaceutical Science Technol 51 (1997) p 2–6.

K. Soderhall et al. "The Effects of β1,3–Glucans on Blood Coagulation and Amebocyte Release in the Horseshoe Crab, *Limulus Polyphemus*" Biol. Bull. 169, 661–674 (Dec. 1985).

A. Kakinuma et al. "Gelation of Limulus Amoebhocyte Lysate by an Antitumor (1→3)–β–D–Glucan" Biochemical and Biophysical Research Communications, vol. 101, No. 2, Jul. 30, 1981, pp. 434–439.

F.C. Pearson et al. "Characterization of Limulus Amoebocyte Lysate–Reactive Material Hollow–Fiber Dialyzer" Applied and Environmental Microbiology, vol. 48, Dec. 1984 p. 1189–1196.

T. Kitagawa et al. "Rapid method for preparing a β–glucan–specific sensitive fraction from Limulus (*Tachypleus tridentatus*) amebocyte lysate" Journal of Chromatography, 567 (1991) 267–273.

T. Obayashi et al. "A new chromogenic endotoxin–specific assay using recombined limulus coagulation enzymes and its clinical applications" Clinica Chimica Acta 149 (1985) 55–65.

Dose Response of Zymosan A with KQCL

The Effect of Cellobiose Concentration on the Glucan LAL Response

ENDOTOXIN-SPECIFIC ASSAY

TECHNICAL AREA OF THE INVENTION

The invention relates to the area of endotoxin detection using an amebocyte lysate. More particularly, the invention relates to the detection of endotoxin using a Limulus amebocyte lysate.

BACKGROUND OF THE INVENTION

Horseshoe crab hemolymph contains an endotoxin-mediated serine protease pathway which causes coagulation of hemolymph in response to endotoxin (lipopolysaccharide) (reviewed in Iwanaga, *Curr. Opin. Immunol.* 5, 74–82, 1993). Limulus amebocyte lysate (LAL) is widely used in assays to detect endotoxin in a variety of test samples, including human and animal pharmaceuticals, biological products, and medical devices. Pharmaceuticals and research products are often tested for contamination from bacterial endotoxins. These contaminants can cause serious side effects if injected into the body, including fever and possibly death.

In an LAL assay, an extract of Limulus amebocytes is mixed with components which confer increased sensitivity and/or stability to the LAL, forming an LAL reagent. A test sample is mixed with the LAL reagent and compared with a series of known endotoxin standards mixed with LAL reagent. Sample and standard results are compared to determine the concentration of endotoxin in the sample.

The LAL assay for endotoxin is not entirely specific. Reaction also occurs in response to β-1,3-glucans, which react with LAL through a separate glucan-sensitive enzymatic pathway (see Iwanaga, 1993). These β-glucans are polymers of glucose, with varying molecular weights and, primarily, β-1,3-glycosidic linkages between the glucose subunits. If a sufficient quantity of a β-glucan is present in a test sample, a false-positive result occurs. A false-positive can result in a manufacturer unnecessarily discarding an expensive medical device or lot of product.

It can often be difficult to determine whether a positive result in the LAL test is due to endotoxin or to β-glucan contamination. Thus, there is a continuing need in the art for endotoxin-specific assays which reduce or eliminate the incidence of false-positive results due to β-glucan contamination.

SUMMARY OF THE INVENTION

It is an object of the invention to provide a means of more specifically detecting endotoxin in a test sample. This and other objects of the invention are provided by one or more of the embodiments described below.

One embodiment of the invention provides a method of inhibiting a glucan-sensitive pathway in an amebocyte lysate suitable for detecting endotoxin in a test sample. The amebocyte lysate is contacted with a β-1,4-glucan in an amount effective to inhibit the glucan-sensitive enzymatic pathway in the amebocyte lysate. All of the glycosidic linkages in the β-1,4-glucan are β-1,4-glycosidic linkages.

Another embodiment of the invention provides a reagent for detecting endotoxin in a test sample. The reagent comprises an amebocyte lysate and a β-1,4-glucan. All of the glycosidic linkages in the β-1,4-glucan are β-1,4-glycosidic linkages.

Yet another embodiment of the invention provides a kit for detecting endotoxin in a test sample. The kit comprises an amebocyte lysate, a β-1,4-glucan, and instructions for using the kit to detect endotoxin. All of the glycosidic linkages in the β-1,4-glucan are β-1,4-glycosidic linkages.

The present invention thus provides the art with reagents and methods for rendering an LAL assay less prone to false positive results due to the presence of glucan contamination and thus more specific for endotoxin detection. The invention can be used, inter alia, to provide an endotoxin-specific assay which avoids false-positive results when a test sample contains trace amounts of β-glucan.

DETAILED DESCRIPTION OF THE PREFERRED EMBODIMENTS

Figure 1:
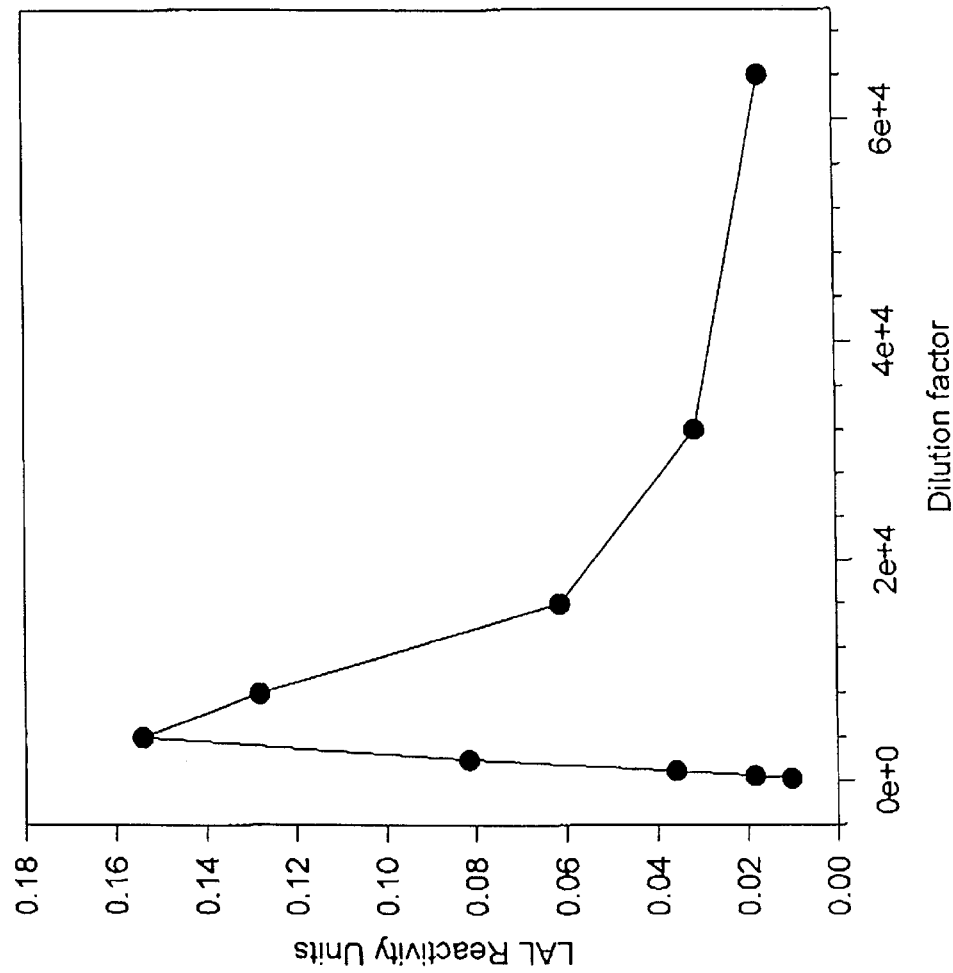
FIG. 1 shows a dose-response curve of a kinetic-chromogenic LAL reagent to different concentrations of LAL-Reactive Material (LAL-RM).

It is a discovery of the present invention that β-glucans in which all of the glycosidic linkages are β-1,4-glycosidic linkages can be used to inhibit the glucan-sensitive pathway in horseshoe crab amebocyte lysates and render LAL reagents and assays specific for endotoxin.

Methods of preparing amebocyte lysates are well known in the art. See, e.g., Levin and Bang, *Bull. Johns Hopkins Hosp.* 115, 265–74, 1968; Young et al., *J. Clin. Invest.* 51, 1790–97, 1972. Amebocyte lysates can be prepared from amebocytes isolated from any species of horseshoe crab, such as *Limulus polyphemus, Tachypleus tridentatus, Tachypleus gigs,* and *Carcinoscorpius rotundicauda.* Amebocyte lysates can be freshly prepared or, as is generally known, can be lyophilized and reconstituted before use. The method of the invention is not to be limited as to the source of lysate. An amebocyte lysate can be in the form of a reagent, suitable for use in, for example, a kinetic-chromogenic, end-point chromogenic, gel-clot, turbidimetric, or enzyme-linked immunosorbent (ELISA) method. Such reagents are disclosed, for example, in U.S. Pat. No. 4,322,217, U.S. Pat. No. 4,510,241, and U.S. Pat. No. 5,310,657. The endotoxin sensitivity range of the lysate is preferably in the range of 0.005 to 50 EU/ml.

Any β-1,4-glucan in which all of the glycosidic linkages are β-1,4-glycosidic linkages can be used in the method of the invention. A dimer (cellobiose) is preferred, but polymers comprising at least 3, 4, 5, 6, 7, 8, 9, or 10 or even more glucose monomer units can also be employed as inhibitors. Optionally, a β-1,4-glucan can comprise one or more chemical moieties, such as alkyl, carboxymethyl, methyl, or hydroxypropyl groups and the like. If the chemical moiety is a glucose monomer or polymer, it is not bound to the β-1,4-glucan by means of a β-1,3- or a β-1,6-glycosidic linkage. If the chemical moiety is a glucose polymer, it does not comprise a β-1,3-glycosidic linkage. A mixture of two or more different β-1,4-glucans, coupled or uncoupled to such chemical moieties, can also be employed according to the invention to inhibit the response of an amebocyte lysate to glucan.

Optimum concentrations of a particular β-1,4-glucan in the assay for inhibiting the glucan-sensitive enzymatic pathway may vary when used with different amebocyte lysate preparations. The amount of a particular β-1,4-glucan which is effective to inhibit the glucan-sensitive enzymatic pathway in a particular source of amebocyte lysate can be determined, for example, by routine testing. Various concentrations of the β-1,4-glucan can be added to an amebocyte lysate assay to which a substance containing β-glucan, such as Zymosan A, has been added, as described in Example 4, below. Preferably, the β-1,4-glucan used as the inhibition-additive according to the invention is cellobiose. An effective amount of cellobiose is expected to range from 100 ng/ml to 100 mg/ml, generally from 100 ng/ml to 70 mg/ml, and most often from 15 mg/ml to 50 mg/ml, 15 mg/ml to 40 mg/ml, 15 mg/ml to 35 mg/ml, or 15 mg/ml to 25 mg/ml (see FIG. 3). Concentrations of cellobiose such as 0.05, 0.1, 0.15, 0.175, 1, 1.5, 2, 2.5, 5, 7.5, 10, 12.5, 15, 17.5, 20, 21, 22, 23, 24, 25, 26, 27, 28, 29, 30, 35, 40, 45, 50, 60, or 70 mg/ml can be used in an amebocyte lysate assay.

According to the invention, an amebocyte lysate is contacted with a β-1,4-glucan. The final reaction mixture comprises an amebocyte lysate, a β-1,4-glucan, and a test sample. However, the amebocyte lysate, β-1,4-glucan, and test sample can be added together in any order. For example, a test sample can be added to an amebocyte lysate-β-1,4-glucan mixture. Or, a test sample can be added to an amebocyte lysate before the amebocyte lysate is contacted with a β-1,4-glucan. The amebocyte lysate and β-1,4-glucan can be lyophilized and reconstituted before the step of contacting. Alternatively, a β-1,4-glucan and a test sample can be premixed before the step of contacting an amebocyte lysate with the β-1,4-glucan. All possible permutations of the order in which a β-1,4-glucan, an amebocyte lysate, and a test sample can be added together are within the scope of the present invention.

The test sample can be any sample in which it would be useful to determine possible endotoxin contamination, including water, medical devices, pharmaceuticals, and biological test samples, such as tissue culture medium, blood, and serum. The response of an amebocyte lysate to a test sample in the presence of a β-1,4-glucan can be detected as is well known in the art. For example, turbidimetric methods, gel-clot formation assays, kinetic-chromogenic methods, end-point chromogenic methods, and enzyme-linked immunosorbent assays are all suitable for use in the method of the invention. Performance of such assays is routine. See, e.g., Morita et al., in BACTERIAL ENDOTOXINS: STRUCTURE, BIOMEDICAL SIGNIFICANCE, AND DETECTION WITH THE LIMULUS AMEBOCYTE LYSATE TEST, pp. 53–64, 1985; Kambayashi et al., *J. Biochem. Biophys. Meth.* 22, 93–100, 1991; Matuura and Tsuchiya, U.S. Pat. No. 5,179,006; and Cooper et al., *PDA J. Pharm. Sci. Technol.* 51, 2–6, 1997. Any method suitable for the particular type of assay employed can be used to detect positive and negative results, including automated readers and software specifically designed to read and calculate the results of an amebocyte lysate assay (e.g., Kinetic-QCL Reader and WinKQCL software, BioWhittaker).

The invention also provides a reagent which can be used to specifically detect endotoxin in a test sample. The reagent comprises an amebocyte lysate, preferably a horseshoe crab amebocyte lysate, most preferably a Limulus amebocyte lysate, and a β-1,4-glucan. The β-1,4-glucan is preferably cellobiose, but can be any polymer comprising two or more glucose monomers, coupled or uncoupled to additional chemical moieties, as described above. The reagent can be provided in lyophilized form, for convenience in storage and transport. Optionally, the reagent can comprise additional components which will confer increased sensitivity or stability in an LAL assay (see U.S. Pat. No. 4,322,217; U.S. Pat. No. 4,510,241; U.S. Pat. No. 5,310,657).

The invention also provides a kit for the specific detection of endotoxin in a test sample. The kit contains an amebocyte lysate, preferably a horseshoe crab amebocyte lysate, most preferably a Limulus amebocyte lysate, and a β-1,4-glucan. The amebocyte lysate can be lyophilized, either together with or separately from the β-1,4-glucan. Preferably, the β-1,4-glucan is cellobiose, but other glucose polymers which are linked by β-1,4-glycosidic bonds, coupled or uncoupled to additional chemical moieties, can be used, as disclosed above. Instructions for using the kit to specifically detect endotoxin can also be included. Optionally, a reagent of the invention, comprising an amebocyte lysate and a β-1,4-glucan, as described above, can be provided in the kit.

The following are provided for exemplification purposes only and are not intended to limit the scope of the invention described in broad terms above.

EXAMPLE 1

This example describes materials and methods which are used in the following examples.

Endotoxin solutions. Purified *E. coli* endotoxin, Reference Standard Endotoxin (RSE) lot EC-6, was obtained from the Center for Biologics Evaluation and Research Center, FDA (Rockville, Md.). One vial containing 10,000 Endotoxin Units was reconstituted with 5.0 ml LAL Reagent Water (LAL-RW) and vortexed for 30 minutes. Serial dilutions of this stock were used to make both the standard and sample preparations.

Native *E. coli* bacteria derived from FDA Strain Seattle 1946, Cat. No. 25922, were obtained from the American Type Culture Collection. Cultures were grown in Trypticase Soy Broth and stored at 2–8° C. prior to testing.

Limulus Amebocyte Lysate Reactive Material (LAL-RM). LAL-RM samples were prepared by rinsing a CF-Capillary Flow Dialyzer, Model CF23, obtained from the Baxter Health Care Corporation (Deerfield, Ill.), with LAL-RW. This rinse was lyophilized and subsequently reconstituted with LAL-RW. LAL-RM samples were stored at <–10° C.

Zymosan A. Zymosan A, from *Saccharomyces cerevisiae*, Cat. No. Z-4250, was obtained from the Sigma Chemical Corporation (St. Louis, Mo.). Zymosan A comprises glucans which contain β-1,3 glycosidic linkages, as well as proteins and lipids. A 5.0 mg sample was mixed with 5 ml of 90% Formic Acid, Cat. No. A-119-500, Fisher Chemical Co. (Fair Lawn, N.J.). This solution was heated to 56° C. until the Zymosan A was completely dissolved (approximately 3 hours). Neutralization of this preparation was achieved by the addition of sodium hydroxide and Tris (hydroxymethyl) aminomethane. The final concentration of Zymosan A in this stock was 317 μg/ml, with a pH of 6.5. This solution was stored at 2–8° C. until use.

Cellobiose. β-D(+)-cellobiose was obtained from either Aldrich Chemical Company (Cat. No. C1,770-5) or Sigma Chemical Company (Cat. No. C-7252). A—cellobiose stock solution was prepared by dissolving cellobiose in LAL-RW and ultrafiltered through an Ultrasart ultrafilter from Sartorius (Cat. No. D20) to remove endotoxin. Ultrafiltered cellobiose was tested and found to contain <0.005 LAL Reactivity Units. Cellobiose preparations were stored at 2–8° C.

EXAMPLE 2

This example demonstrates titration of LAL-RM, in order to find an optimal amount of LAL-RM for use in later testing.

The LAL-RM preparation was diluted with LAL-RW and tested using a freeze-dried Limulus Amebocyte Lysate (LAL) reagent, marketed by BioWhittaker as Kinetic-QCL (KQCL BioWhittaker Kinetic-QCL Reagent #K50-643). The reagent was prepared as described in U.S. Pat. No. 5,310,657. This preparation had a linear response to endotoxin in the range of 0.005–50 EU/mL. KQCL Reagent was reconstituted with either 2.6 ml of LAL-RW or 2.6 ml of cellobiose dissolved in LAL-RW.

Testing described in this and in subsequent examples was carried out under conditions that minimized endotoxin contamination. A series of endotoxin standards were prepared using the 2000 EU/ml EC-6 stock. Standard concentrations of 0.005, 0.05, 0.50, 5.0, and 50 EU/ml were included in all tests.

Standards or samples (100 μl) were added to a 96-well microplate. The microplate was placed in an incubating microplate reader designed to perform endotoxin testing (Kinetic-QCL Reader #25-141B, BioWhittaker, Inc.). After pre-incubating the plate for 10 minutes, 100 μl of KQCL with or without cellobiose were added to appropriate wells of the microplate. The microplates were shaken for 30 seconds.

Software specifically designed to perform endotoxin testing was utilized to run the test and perform data analysis (WinKQCL #25-300, BioWhittaker, Inc.). Sample results were reported as "LAL Reactivity Units," which is the LAL activity measured against the EC-6 standard curve. The results are shown in FIG. 1.

A typical bell-shaped curve was observed. Maximum activity of the KQCL Reagent was seen at a 1:4000 dilution of LAL-RM. Higher concentrations of LAL-RM resulted in lower values, typical of the "saturation effect" when excess β-glucans are present in an LAL assay.

EXAMPLE 3

This example demonstrates dose-response of the LAL assay to Zymosan A, in order to find an optimal amount of Zymosan A for use in later testing.

Figure 2:
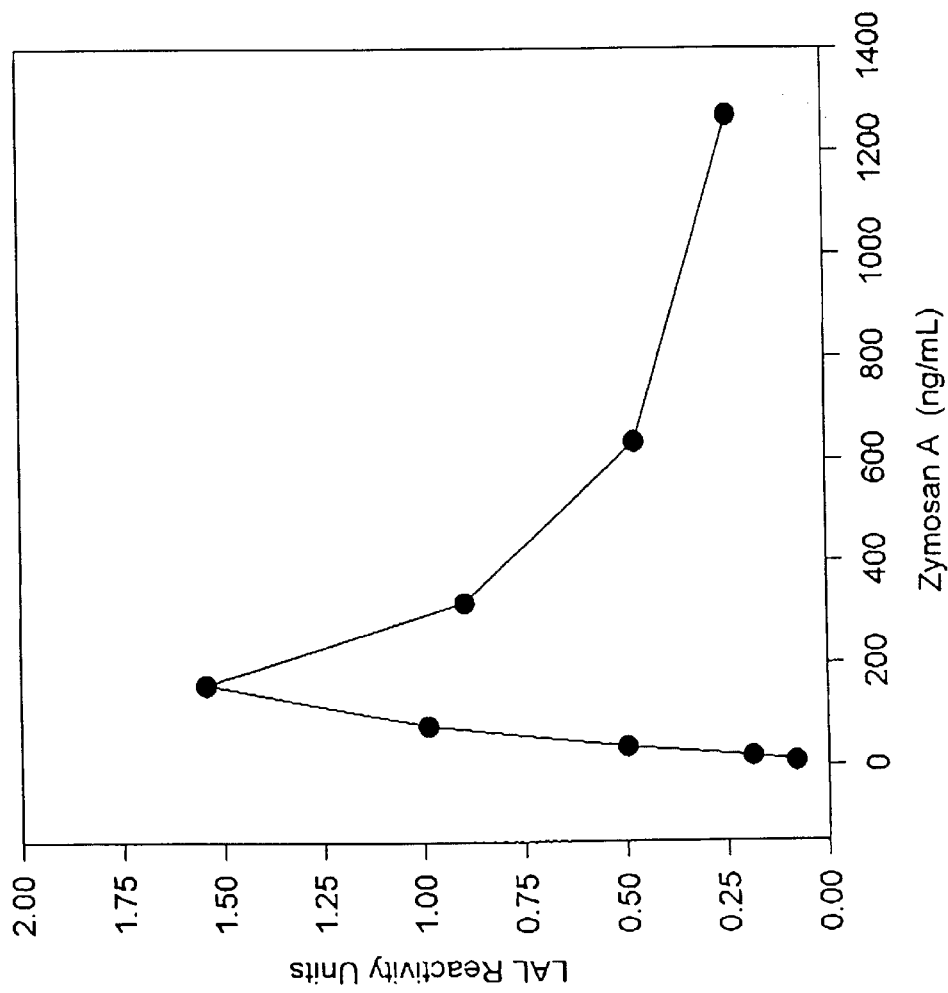
FIG. 2 shows a dose-response curve of a kinetic-chromogenic LAL reagent to different concentrations of Zymosan A.

The Zymosan A preparation (317 μg/ml) was diluted in LAL-RW and tested using BioWhittaker KQCL Reagent K50-643, as described in Example 2, above. The results are shown in FIG. 2.

A typical bell-shaped response curve was observed. Maximum activity was seen at 159 ng/ml of Zymosan A Higher concentrations of Zymosan A resulted in lower values, typical of the "saturation effect" when excess β-glucans are present in an LAL assay.

EXAMPLE 4

This example demonstrates comparative testing to find an optimum amount of cellobiose for use in later testing.

Figure 3:
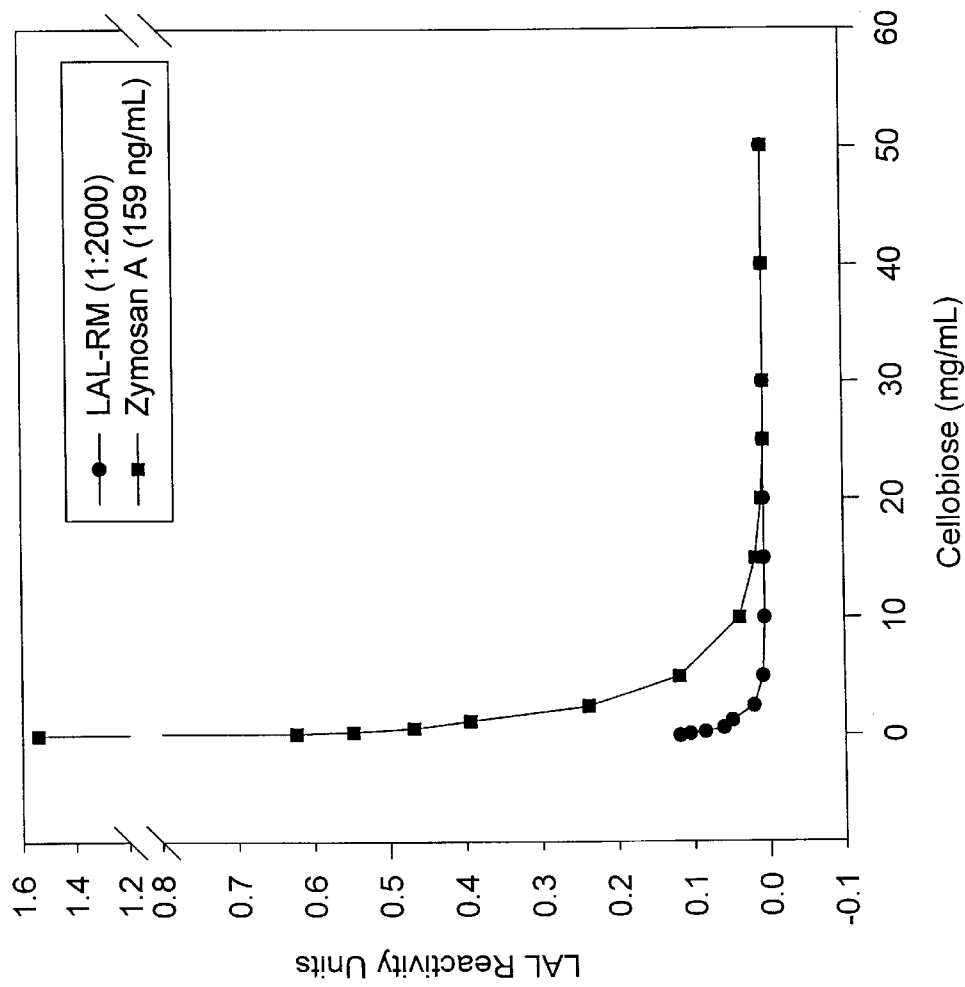
FIG. 3 shows dose-response curves of a kinetic-chromogenic LAL reagent to LAL-RM and to Zymosan A in the presence of varying concentrations of cellobiose.

Preparations of LAL-RM and Zymosan A were tested with KQCL Reagent reconstituted with LAL-RW and KQCL reconstituted with varying concentrations of cellobiose (see FIG. 3). Each preparation was tested at the dilution or concentration that gave maximal reactivity in a KQCL assay as determined in Examples 2 (FIG. 1) and 3 (FIG. 2), above.

The addition of cellobiose to the KQCL Reagent inhibited the response to the glucans present in both the LAL-RM and Zymosan A preparations. The minimum concentration of cellobiose tested (0.156 mg/ml) had little effect as a glucan inhibitor. Total inhibition was observed at as low a cellobiose concentration as about 25 mg/ml. Testing of EC-6 endotoxin with KQCL Reagent reconstituted with LAL-RW or KQCL Reagent reconstituted with cellobiose demonstrated the specificity of both reagents to endotoxin.

These results indicate that preparations of endotoxin can be assayed in a kinetic-chromogenic LAL assay without interference from glucans by the addition of an optimal amount of cellobiose.

EXAMPLE 5

This example demonstrates that cellobiose inhibits the response of an LAL assay to glucan contamination when added to a previously prepared lyophilized LAL reagent.

A comparison was performed between the KQCL Reagent and KQCL Reagent reconstituted with 35 mg/ml cellobiose. Both preparations were used to test samples of LAL-RW, purified EC-6 endotoxin, native *E. coli* bacteria, LAL-RM, and Zymosan A samples. Results are shown in Table 1.

TABLE 1

| | LAL Reactivity Units | |
| --- | --- | --- |
| Sample | KQCL Reagent alone | KQCL Reagent and 35 mg/ml cellobiose |
| LAL-RW | <0.005 | <0.005 |
| EC-6 endotoxin | 0.508 | 0.532 |
| Native *E. coli* endotoxin | 0.814 | 0.838 |
| LAL-RM* | 0.160 | <0.005 |
| Zymosan A** | 1.58 | <0.005 |

*LAL-RM = 1:5000 dilution
**Zymosan A = 159 ng/ml

The LAL-RW preparation tested negative (<0.005 LAL Reactivity Units) with both reagents. Both reagents showed a similar response to the purified EC-6 and native *E. coli* samples. Significant differences were seen when testing the LAL-RM or Zymosan A samples with the two reagents. The KQCL Reagent showed positive results when tested with either LAL-RM or Zymosan A. In contrast, no LAL reactivity was seen to either LAL-RM or Zymosan A using KQCL Reagent reconstituted with cellobiose.

These results indicate that test samples can be assayed for endotoxin in a kinetic-chromogenic assay without interference from glucan contamination or impurities by including an effective amount of cellobiose in the reaction mixture.

EXAMPLE 6

This example demonstrates that cellobiose effectively inhibits the response of a kinetic-chromogenic LAL reagent to glucans if co-lyophilized with the LAL reagent.

A comparison was performed between the KQCL Reagent and a reagent of the invention by prepared by co-lyophilizing the KQCL Reagent with 35 mg/ml cellobiose. Both preparations were used to test samples of LAL-RW, purified EC-6 endotoxin, native *E. coli* endotoxin, LAL-RM (1:2000), and Zymosan A 159 ng/ml) samples. The results are shown in Table 2.

TABLE 2

| | LAL Reactivity Units | |
|---|---|---|
| Sample | KQCL Reagent alone | KQCL Reagent and 35 mg/ml cellobiose |
| LAL-RW | <0.005 | <0.005 |
| EC-6 endotoxin | 0.541 | 0.508 |
| Native *E. coli* endotoxin | 0.868 | 1.05 |
| LAL-RM* | 0.16 | <0.005 |
| Zymosan A** | 1.12 | <0.005 |

*LAL-RM = 1:5000 dilution
**Zymosan A = 159 ng/ml

Both reagents showed a similar response to the purified EC-6 and native *E. coli* samples. However, in the presence of cellobiose, no LAL reactivity was measured in the LAL-RM or Zymosan A samples. These results indicate that preparations of endotoxin can be assayed without interference from glucans by adding an effective amount of cellobiose. Additionally, the cellobiose can be added to an LAL reagent, such as the KQCL Reagent used in this example, and then lyophilized.

EXAMPLE 7

This example demonstrates that cellobiose similarly blocks a glucan response in a turbidimetric LAL endotoxin assay.

A turbidimetric LAL assay was performed using the turbidimetric LAL reagent Pyrogent® 5000 (BioWhittaker, Catalog Nos. N383, N384), as described in the accompanying instruction brochure. The response of the assay to LAL-RW, purified EC-6 endotoxin, native *E. coli* endotoxin, LAL-RM, and Zymosan A was measured in the presence or absence of 35 mg/ml cellobiose. The results are shown in Table 3.

TABLE 3

| | LAL Reactivity Units | |
|---|---|---|
| Sample | Pyrogent® 5000 alone | Pyrogent® 5000 and 35 mg/ml cellobiose |
| LAL-RW | <0.01 | <0.01 |
| EC-6 endotoxin | 1.96 | 2.22 |
| Native *E. coli* endotoxin | 1.81 | 1.86 |
| LAL-RM* | 0.012 | <0.01 |
| Zymosan A** | 0.217 | <0.01 |

*LAL-RM = 1:5000 dilution
**Zymosan A = 159 ng/ml

Positive results were obtained to both purified EC-6 endotoxin and native *E. coli* endotoxin, in either the presence or absence of cellobiose. In the absence of cellobiose, however, positive results were obtained in response to both LAL-RM and Zymosan A. The presence of cellobiose in the assay inhibited the response of the Pyrogent® 5000 reagent to LAL-RM and Zymosan A.

These results indicate that the glucan-responsive pathway in an LAL can be inhibited by the presence of cellobiose in an LAL turbidimetric assay.

EXAMPLE 8

This example demonstrates that cellobiose blocks a glucan response in a gel-clot endotoxin assay.

The response of the assay to LAL-RW, purified EC-6 endotoxin, native *E. coli* endotoxin, LAL-RM, and Zymosan A was measured in a gel-clot assay in the presence or absence of 35 mg/ml cellobiose. A positive result was recorded if a firm gel was created in the bottom of the test tube and the gel remained intact when the tube was inverted 180°. The results are shown in Table 4.

TABLE 4

| Sample | LAL | LAL and 35 mg/ml cellobiose |
|---|---|---|
| LAL-RW | − | − |
| EC-6 (0.03 EU/ml) | + | + |
| Native *E. coli* endotoxin | + | + |
| LAL-RM* | + | − |
| Zymosan A** | + | − |

*LAL-RM = 1:5000 dilution
**Zymosan A = 159 ng/ml

Positive results were obtained to both purified EC-6 endotoxin and native *E. coli* endotoxin, in either the presence or absence of cellobiose. In the absence of cellobiose, however, gel-clots were formed in response to both LAL-RM and Zymosan A. The presence of cellobiose in the assay inhibited gel-clot formation in response to LAL-RM and Zymosan A.

These results indicate that the glucan-responsive pathway in an LAL can be inhibited by the presence of cellobiose in a gel-clot assay.

I claim:

1. A method for reducing the number of false positives in an endotoxin assay due to a glucan-sensitive enzymatic pathway in an amebocyte lysate, comprising the step of:

contacting said amebocyte lysate with a β-1,4-glucan in an amount effective to inhibit said glucan-sensitive enzymatic pathway in the amebocyte lysate, wherein all of the glycosidic linkages of the β-1,4-glucan are β-1,4-glycosidic linkages.

2. The method of claim 1 wherein the β-1,4-glucan is a polymer comprising two or more glucose monomers.

3. The method of claim 2 wherein the β-1,4-glucan is cellobiose.

4. The method of claim 3 wherein the effective amount of cellobiose is 100 ng/ml to 100 mg/ml.

5. The method of claim 3 wherein the effective amount of cellobiose is 100 ng/ml to 70 mg/ml.

6. The method of claim 3 wherein the effective amount of cellobiose is 15 mg/ml to 50 mg/ml.

7. The method of claim 3 wherein the effective amount of cellobiose is 15 mg/ml to 40 mg/ml.

8. The method of claim 3 wherein the effective amount of cellobiose is 15 mg/ml to 35 mg/ml.

9. The method of claim 3 wherein the effective amount of cellobiose is 15 mg/ml to 25 mg/ml.

10. The method of claim 1 wherein at least one of the hydroxyls of the β-1,4-glucan have been modified by a chemical group selected from the group consisting of an alkyl, a carboxymethyl, a methyl, and a hydroxylpropyl moiety.

11. The method of claim 1 wherein the β-1,4-glucan and the test sample are pre-mixed before the step of contacting the amebocyte lysate.

12. The method of claim 1 wherein the test sample is added to the amebocyte lysate before the step of contacting the amebocyte lysate.

13. The method of claim 1 wherein the test sample is added to the amebocyte lysate after the step of contacting the amebocyte lysate.

14. The method of claim 1 wherein the amebocyte lysate is prepared from amebocytes of a horseshoe crab selected from the group consisting of *Limulus polyphemus, Tachypleus tridentatus, Tachypleus gigas,* and *Carcinoscorpius rotundicauda.*

15. The method of claim 1 wherein the amebocyte lysate has been lyophilized and reconstituted before the step of contacting the amebocyte lysate.

16. The method of claim 1 wherein the amebocyte lysate has been lyophilized and reconstituted after the step of contacting the amebocyte lysate.

17. In a method for measuring endotoxin in a test sample using an amebocyte lysate, the improvement which comprises the step of:

contacting an amebocyte lysate suitable for detecting endotoxin in a test sample with a β-1,4-glucan in an amount effective to inhibit the glucan-sensitive enzymatic pathway in the amebocyte lysate, wherein all of the glycosidic linkages of the β-1,4-glucan are β-1,4-glycosidic linkages, wherein the endotoxin in the test sample is detected by a method selected from the group consisting of a kinetic-chromogenic method, an endpoint chromogenic method, a gel-clot method, a turbidimetric method, and an enzyme-linked immunosorbent assay method.

18. A reagent for specifically detecting the presence of an endotoxin in a test sample, comprising:

an amebocyte lysate; and a β-1,4-glucan, wherein all of the glycosidic linkages in the β-1,4-glucan are β-1,4-glycosidic linkages.

19. The reagent of claim 18 wherein the β-1,4-glucan is a polymer comprising two or more glucose monomers.

20. The reagent of claim 19 wherein the β-1,4-glucan is cellobiose.

21. The reagent of claim 18 wherein the reagent is lyophilized.

22. A kit for detecting the presence of endotoxin in a test sample, comprising:

an amebocyte lysate;

a β-1,4-glucan, wherein all of the glycosidic linkages in the β-1,4-glucan are β-1,4-glycosidic linkages; and instructions for using the kit to detect endotoxin.

23. The kit of claim 22 wherein the β-1,4-glucan is a polymer comprising two or more glucose monomers.

24. The kit of claim 23 wherein the β-1,4-glucan is cellobiose.

* * * * *

UNITED STATES PATENT AND TRADEMARK OFFICE
CERTIFICATE OF CORRECTION

PATENT NO. : 5,998,389
DATED : December 7, 1999
INVENTOR(S) : Bruce LOVEROCK

It is certified that error appears in the above-identified patent and that said Letters Patent is hereby corrected as shown below:

Claim 10, column 8, line 55, delete "have" and insert --has--.

Signed and Sealed this

Seventeenth Day of October, 2000

Attest:

Q. TODD DICKINSON

*Attesting Officer*  *Director of Patents and Trademarks*